United States Patent
Grande et al.

(10) Patent No.: US 10,610,458 B2
(45) Date of Patent: Apr. 7, 2020

(54) ORTHODONTIC ADHESIVES AND METHODS OF USING SAME

(71) Applicant: Ormco Corporation, Orange, CA (US)

(72) Inventors: Jessica Elivier Grande, Chino, CA (US); Sammel Shahrier Alauddin, Rancho Cucamonga, CA (US)

(73) Assignee: Ormco Corporation, Orange, CA (US)

( * ) Notice: Subject to any disclaimer, the term of this patent is extended or adjusted under 35 U.S.C. 154(b) by 0 days.

(21) Appl. No.: 15/699,230

(22) Filed: Sep. 8, 2017

(65) Prior Publication Data
US 2019/0076334 A1    Mar. 14, 2019

(51) Int. Cl.
*A61K 6/00*    (2020.01)
*A61C 7/16*    (2006.01)
(Continued)

(52) U.S. Cl.
CPC ............... *A61K 6/0023* (2013.01); *A61C 7/16* (2013.01); *A61K 6/0029* (2013.01);
(Continued)

(58) Field of Classification Search
CPC .......... A61K 6/0023; A61C 7/16; C08K 5/13; C08L 33/08; C08L 33/10; C08L 33/12;
(Continued)

(56) References Cited

U.S. PATENT DOCUMENTS

| 7,622,550 B2 | 11/2009 | Cha et al. |
| 8,563,117 B2 | 10/2013 | Messersmith et al. |

(Continued)

FOREIGN PATENT DOCUMENTS

| CN | 103610598 B | 12/2015 |
| WO | WO 2017/132463 | * 8/2017 |
| WO | WO 2017/132484 | * 8/2017 |

OTHER PUBLICATIONS

Shafiq et al., "Bioinspired Underwater Bonding and Debonding on Demand," 51 Angew.Chem. Int. Ed. 4332-35 (2012).
(Continued)

*Primary Examiner* — C Melissa Koslow
(74) *Attorney, Agent, or Firm* — Wood Herron & Evans LLP

(57) ABSTRACT

An orthodontic adhesive includes components capable of allowing easy debonding of an orthodontic device from a patient's tooth. The adhesive includes an engineered marine mussel protein. The adhesive may include at least one photocleavable moiety. The adhesive is applied in one or more individual layers. One of the components of the adhesive is capable of binding to a tooth and the other component may be capable of binding to an orthodontic device. A method of adhering an orthodontic device to a tooth includes applying a layer of an orthodontic adhesive to either the tooth or the orthodontic device or the tooth and the orthodontic device and affixing the orthodontic device to the tooth with the orthodontic adhesive situated between the tooth and the orthodontic device. The engineered marine mussel protein includes one or more catechol moieties or one or more derivatives of a catechol moiety.

9 Claims, 8 Drawing Sheets

(51) Int. Cl.
    *A61L 31/04*     (2006.01)
    *C08K 5/13*     (2006.01)
    *C08L 33/12*     (2006.01)
    *C09J 133/12*     (2006.01)
    *C09J 189/00*     (2006.01)

(52) U.S. Cl.
    CPC .............. *A61L 31/043* (2013.01); *C08K 5/13* (2013.01); *C08L 33/12* (2013.01); *C09J 133/12* (2013.01); *C09J 189/00* (2013.01)

(58) Field of Classification Search
    CPC ...... C09J 138/08; C09J 138/10; C09J 138/12; C09J 198/00
    See application file for complete search history.

(56) References Cited

U.S. PATENT DOCUMENTS

| | | |
|---|---|---|
| 2005/0215034 A1 | 9/2005 | Vandroux et al. |
| 2013/0228735 A1 | 9/2013 | Higuchi et al. |
| 2016/0160097 A1 | 6/2016 | Waite et al. |
| 2017/0217999 A1* | 8/2017 | Ahn ........................ C07C 69/01 |

OTHER PUBLICATIONS

U.S. Department of the Interior, Reclamation: Managing Water in the West, Technical Memorandum No. MERL_2013-43, "Review of Mussel Adhesion Mechanism and Scoping Study," Aug. 2013.
Dental Tribune International, "Mussels help researchers develop tougher restorative product: Dental Tribune Amerca," Sep. 6, 2017.
Internatonal Searching Authority, International Search Report and Written Opinion in corresponding PCT/US2018/049937 dated Jan. 8, 2019.
Sang-Bae Lee et al., "Cathechol-Functionalized Synthetic Polymer as a Dental Adhesive to Contaminated Dentin Surface for a Composite Restoration", Biomacromolecules, vol. 16, No. 8, Jul. 31, 2015, pp. 2265-2275.
Sungbaek Seo et al., "Significant Performance Enhancement of Polymer Resins by Bioinspired Dynamic Bonding", Advanced Materials, vol. 29, No. 39, Aug. 18, 2017.
Theodore Eliades: "Orthodontic materials research and applications: Part 1. Current status and projected future developments in bonding and adhesives", American Journal of Orthodontics and Dentofacial Orthopedics, vol. 130, No. 4, 2006, pp. 445-451.
Zhang Hong et al., "Mussel-inspired hyperbranched poly(amino ester) polymer as strong wet tissue adhesive", Biomaterials, vol. 35, No. 2, 2014, pp. 711-719.

* cited by examiner

ORTHODONTIC ADHESIVES AND METHODS OF USING SAME

FIELD

The present invention is generally related to the field of orthodontic adhesives, adhesive systems, and methods of using those adhesives.

BACKGROUND

Current orthodontic treatment with orthodontic brackets or other devices that may be attached to the patient's teeth may require the enamel to be prepared prior to attachment of the device to the tooth. Preparation of the tooth surface may be through a series of steps including cleaning, acid etching, and sealing, with intermediate rinse and dry steps, before the clinician may apply an adhesive. For example, to bond a bracket to tooth enamel, each tooth is first cleaned with a slurry of abrasive, such as pumice, to remove pellicle from the enamel. Then, after rinsing and drying the cleaned surface, a phosphoric acid etchant is carefully placed on the surface locations of the tooth to which the clinician desires to attach the orthodontic device. The acid etching step demineralizes the enamel surface and removes a layer of approximately 30 μm or so of hydroxyapatite from the enamel rods. After between 30 and 90 seconds of etch time, the etchant is rinsed away with a water spray and a high flow evacuator. In this way, etching provides a porous structure.

Following the drying step after etching, a sealant (e.g., Ortho Solo™ sealant) is applied to the etched surface. The sealant may penetrate the porous, acid etched surface. Once the sealant cures, a mechanical interlock is created between the tooth and the sealant. An adhesive (e.g., Enlight) and the bracket may be pressed onto the sealed surface with the adhesive between the bracket and the sealant. The adhesive may be a composite resin paste adhesive that includes a mixture of methacrylate monomers, a photo-initiator, and a glass/hydroxyapatite powder. Once the adhesive cures, it secures the bracket to the sealant. This bonding arrangement results in a sandwich-like construction with the sealant and the adhesive sandwiched between the tooth surface and the orthodontic bracket. This procedure and bonding arrangement is then repeated for each tooth that will receive an orthodontic device and so, in the case of orthodontic brackets and molar tube, this may involve 28 teeth per patient.

The current preparation process has many drawbacks. From the perspective of the clinician, it is a manually time-intensive process. It is not surprising that office chair time during the entire bonding procedure is lengthy. Overall, bonding orthodontic brackets to teeth is costly. From the patient's perspective, the process is uncomfortable and enamel removal is often irreversible due to the difficulty of remineralizing dental hard tissues. Thus, the tooth surface may be permanently compromised by acid etching. Certain patients may have an allergic reaction to the etchant. Liquid etchant may flow to the gingiva where it may irritate the soft tissue. Gel etchant, despite allowing more precise placement, requires skillful application and is more difficult to remove. In either application, when the etchant must be rinsed away, care must be taken not to splash or wash the etchant in a manner that may harm the patient or clinician, but the rinsing must be thorough so that the etching reaction is terminated and there is no residual acid or mineral debris that hinders the mechanical interlock between the tooth and the device.

During treatment, the decalcification of the enamel surface adjacent to fixed orthodontic appliances is prevalent. Decalcification is manifested as a white spot lesion (WSL). If left untreated, WSL may progress to produce carious cavitations, and may also present aesthetic problems. Thus, the prevention, diagnosis, and treatment of WSLs is crucial to minimize tooth decay as well as tooth discoloration that could compromise the aesthetics of the patient's smile. However, the problems and costs don't end with bonding.

After orthodontic treatment is complete, the clinician must remove the orthodontic bracket from each tooth. This debonding process requires the clinician to break the bond formed during the bonding process. Mechanically fracturing the bond may require significant skill on the part of the clinician if the patient is to avoid pain. Even with orthodontic brackets that include design features for easier debonding, considerable adhesive/sealant residue may be left on the tooth surface after removal of the bracket. This residue must be mechanically removed with a dental bur, which is an extremely uncomfortable process for the patient and is tedious for the clinician.

Therefore, a need exists for orthodontic adhesives, adhesive systems, and methods of using those adhesives and systems, that do not require the complex pre-attachment treatment described above and that reduce issues associated with debonding orthodontic devices from teeth.

SUMMARY OF THE INVENTION

The present invention overcomes the foregoing and other shortcomings and drawbacks of orthodontic adhesives heretofore known. While the invention will be described in connection with certain embodiments, it will be understood that the invention is not limited to these embodiments. On the contrary, the invention includes all alternatives, modifications and equivalents as may be included within the spirit and scope of the present invention.

In one aspect, an orthodontic adhesive system comprises an engineered marine mussel protein. The engineered marine mussel protein includes at least one catechol moiety or catechol derivative moiety.

In one embodiment, the adhesive system further comprises a nitrocatechol derivative. In one embodiment, the nitrocatechol derivative is nitrodopamine, and in one embodiment, the nitrocatechol derivative is nitronorepinephrine. In one embodiment, the nitrocatechol derivative is nitroepinephrine.

In one embodiment, the engineered marine mussel protein includes catechol-methacrylate.

In one embodiment, the orthodontic adhesive includes a photocleavable bis-methacrylate.

In another aspect of the invention, a method of adhering an orthodontic device to a tooth comprises applying a layer of an orthodontic adhesive to the tooth and/or the orthodontic device. The orthodontic adhesive comprises an engineered marine mussel protein. The method further includes affixing the orthodontic device to the tooth with the orthodontic adhesive situated between the tooth and the orthodontic device.

In one embodiment, the engineered marine mussel protein includes a catechol moiety or one or more derivatives of a catechol moiety and applying the layer includes the catechol moiety or one or more derivatives of the catechol moiety to the tooth.

In one embodiment, the catechol moiety includes catechol-methacrylate.

In one embodiment, the method further comprises applying an acrylate moiety and/or a methacrylate moiety onto the layer. In one embodiment, the moiety is bis-methacrylate.

In another aspect of the invention, an attachment for use with an aligner during orthodontic treatment comprises an engineered marine mussel protein.

In another aspect of the invention, a kit comprises an orthodontic device and an engineered marine mussel protein.

BRIEF DESCRIPTION OF THE DRAWINGS

The accompanying drawings, which are incorporated in and constitute a part of this specification, illustrate embodiments of the invention and, together with a detailed description given below, serve to explain the principles of the invention.

DETAILED DESCRIPTION

In this Detailed Description, all references to the Periodic Table of the Elements refer to the Periodic Table of the Elements, published and copyrighted by CRC Press, Inc., 2001. Also, any reference to a Group or Groups shall be to the Group or Groups as reflected in this Periodic Table of the Elements using the IUPAC system for numbering groups. As used herein, the term "(poly)" means optionally more than one, or stated alternatively, one or more.

Figure 1:
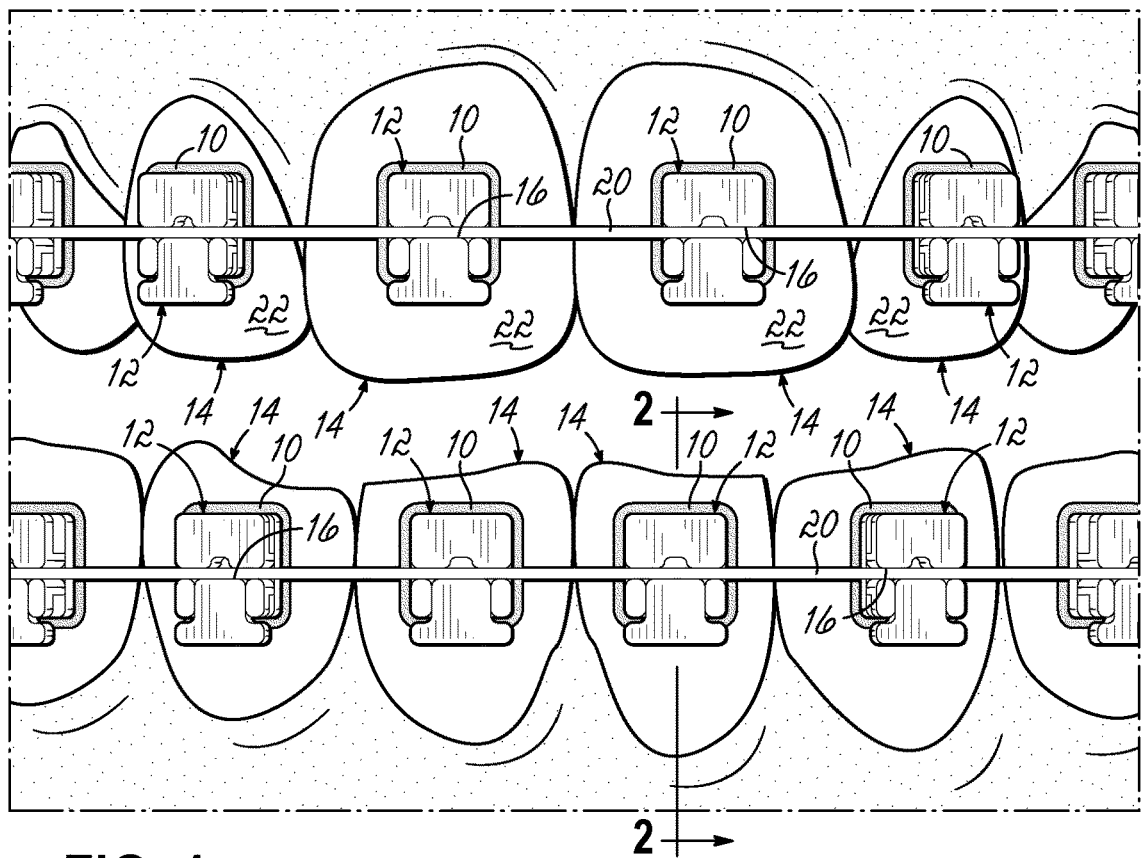
FIG. 1 shows a set of orthodontic brackets with individual brackets attached to the teeth of a patient.
Figure 2:
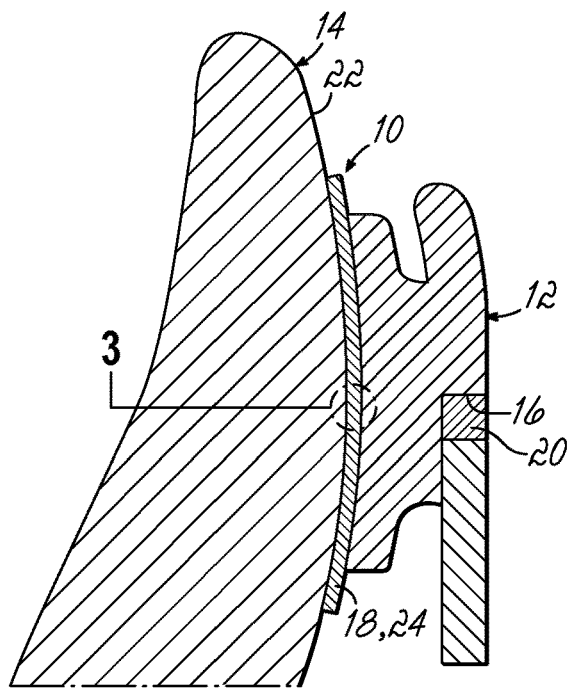
FIG. 2 is a cross-sectional view taken along section line 2-2 of FIG. 1.

To address these and other issues, in one embodiment, a clinician may utilize an orthodontic adhesive system 10 to adhere an orthodontic device to a patient's tooth. As described in detail below, the orthodontic adhesive system 10 includes an engineered protein. By way of example only, as shown in FIG. 1, an orthodontic bracket 12 may be used in an orthodontic procedure. One orthodontic bracket 12 may be affixed to each of a plurality of teeth 14 with the orthodontic adhesive system 10. The orthodontic bracket 12 defines a substantially transversely disposed archwire slot 16, which receives an archwire 20. The orthodontic bracket 12 may be adhesively secured to an exterior facing surface 22 with the orthodontic adhesive system 10. Although not shown in FIG. 1, the orthodontic adhesive system 10 may be between each of the orthodontic brackets 12 and the corresponding tooth 14. While brackets 12 are shown and described herein, embodiments of the present invention may be utilized to bond other orthodontic appliances to the patient's teeth. For example, the orthodontic adhesive system 10 may be utilized to bond a lingual retainer and bite turbos, to name a few, to the patient's teeth.

Figure 3:
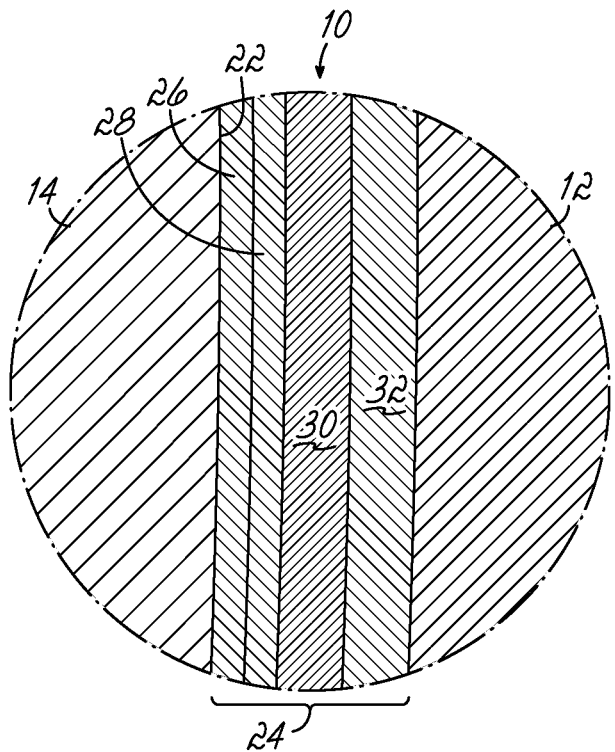
FIG. 3 is an enlarged view of an encircled area 3 of FIG. 2 according to one embodiment of the invention.
Figure 4:
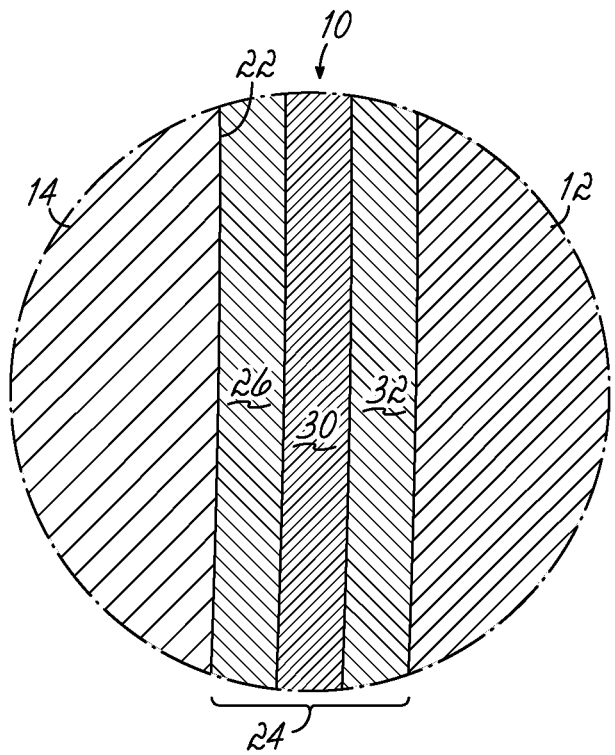
FIG. 4 is an enlarged view of an encircled area 3 of FIG. 2 according to one embodiment of the invention.
Figure 5:
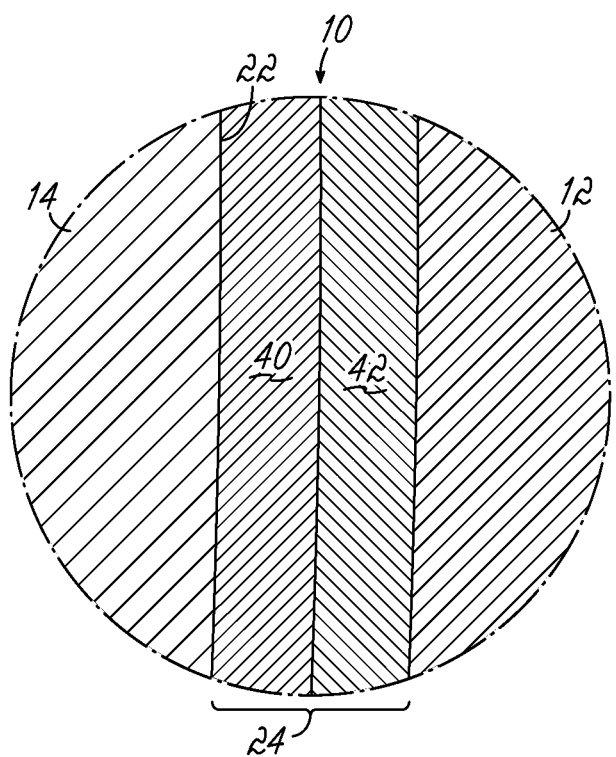
FIG. 5 is an enlarged view of the encircled area 3 of FIG. 2 according to one embodiment of the invention.
Figure 6:
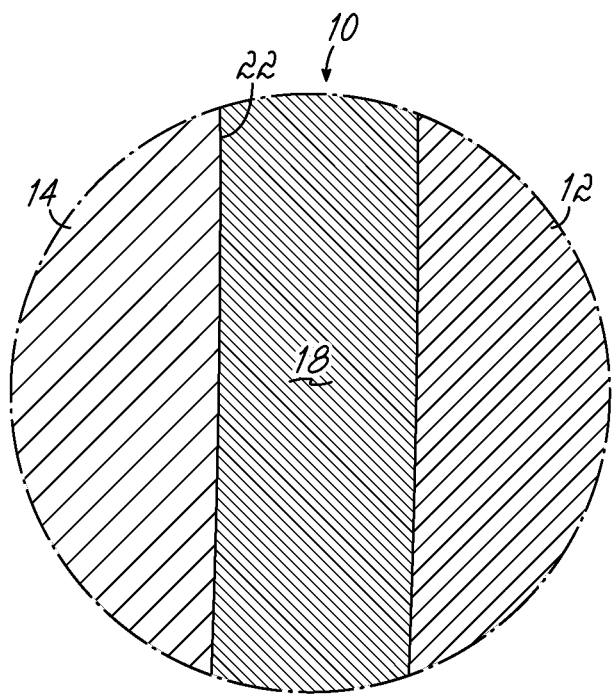
FIG. 6 is an enlarged view of the encircled area 3 of FIG. 2 according to one embodiment of the invention.

With reference to FIGS. 2-6, the orthodontic adhesive system 10 may include a single layer 18 of one or more components as is shown in FIG. 6 or a plurality of layers 24 of individual, separately-applied components, as is shown in FIGS. 3-5. While the plurality of layers 24 appear to be illustrated in equal parts in FIGS. 3-5, this is not necessary to the invention. In accordance with the present invention, the plurality of layers 24 of individual, separately-applied components may be of differing dimensions and thicknesses in relation to each other. The layers 18, 24 include one or more components that are configured to bond to one of the tooth surface 22 or an orthodontic appliance 12 or form a bond between other components in a sandwich-like composite construction. When attached to respective teeth 14 with the orthodontic adhesive system 10, the brackets 12 and the archwire 20 collectively provide orthodontic treatment.

According to the embodiments of the invention, the orthodontic adhesive system 10 may eliminate one or more of the tooth preparation steps described above. For example, the orthodontic adhesive system 10 may not require one or more of the cleaning and acid etching steps, described above, though the system 10 secures the orthodontic bracket 12 to a corresponding tooth 14. Furthermore, the orthodontic adhesive system 10 may improve the ease with which the orthodontic bracket 12 may be intentionally removed from the tooth 14. Thus, orthodontic adhesive systems 10 according to embodiments of the invention may not require significant application of mechanical force to debond the bracket 12 from the tooth 14, and so patients will not experience the discomfort during removal.

Following removal of the orthodontic bracket 12, there will be minimal, if any, adhesive residue on the tooth 14. Embodiments of the invention will therefore also eliminate or minimalize post-removal cleaning of the teeth 14. As another benefit to the patient, the orthodontic adhesive system 10 will eliminate or minimalize demineralization issues created by acid etching during preparation of the tooth surface. The orthodontic adhesive system 10 according to embodiments of the invention may have self-healing properties so that the orthodontic adhesive system 10 resists aging and long-term degradation. As another advantage to both the patient and clinician, the system 10 may allow reversible bonding and debonding of the device 12 to the tooth 14. That is, a bonding network of the orthodontic adhesive system 10 may be selectively activated to bond and deactivated to debond with the surface of the tooth 14 or from the orthodontic device 12. A clinician may then easily correct the orientation of a misplaced device.

A complicating factor for orthodontic adhesives is the environment to which the adhesive is exposed. The mouth of the patient is filled with saliva, which is an aqueous solution of electrolytes, enzymes, and cellular matter. This environment necessitates the complicated tooth preparation process and bonding process, described above, to produce a mechanical bond between the tooth and the orthodontic device.

Applicants identified that the oral environment has similarities to seawater, which is a solution of water, electrolytes, and biological material. In the ocean, mussels possess a remarkable ability to attach and detach themselves from surfaces that are submersed in seawater. Applicants have found that using an engineered marine mussel protein or similar protein as a component in the orthodontic adhesive system 10 will provide sufficient bond strength between an orthodontic device, such as the orthodontic bracket 12, and a tooth 14. Bonding may be accomplished in the absence of the complicated preparation and bonding process described above. Embodiments of the orthodontic adhesive system 10 include selected engineered mussel proteins or similar components to mimic the attachment and/or detachment functionality of the mussel in the oral environment. The engineered mussel protein is synthetically produced.

Marine mussels secrete a glue-like sticky material, known as byssus, which is responsible for the strong adhesion to rocks and other surfaces in turbulent marine environment. The byssus is a bundle of thread-like materials that spreads out in a radially outward direction. It consists of four parts, namely, plaque, thread, stem, and root. Mussel byssus is proteinaceous. In other words, mussel byssus is a protein derived from marine mussels. Byssal threads are attached to the root at the base of mussel foot where a combination of 12 retractor muscles controls the tension in them. More than 25 different mussel foot proteins (mfp) have been identified in byssus, out of which 5 (mfp-2 to mfp-6) are unique to plaque. These 5 mfp have a high content of the usually rare modified amino acid 3,4-dihydroxy-L-phenylalanine (hereinafter "DOPA") (1).

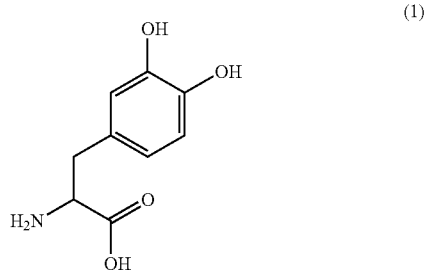 [SMILES: NC(Cc1ccc(O)c(O)c1)C(=O)O]

(1)

As shown in (1) above, DOPA includes a catechol moiety. When combined with oxidant cations from seawater under basic pH conditions, catechol oxidation of the catechol moiety of DOPA produces quinine. The quinine can form a cross-linked polymer matrix in the bonding network. Further, when bonding to rocks, the catechol moiety of DOPA may undergo chelation with inorganic oxides found in the rock. Cohesion between molecules of DOPA is aided by multivalent cations, such as $Fe^{3+}$ and $Ca^{2+}$ ions. These cations form metal complexes between non-oxidized catechols of DOPA and facilitate wet adhesion of the bonding network in seawater. It has been found that it is the catechol functionality of DOPA that gets attached with external surface during the adhesion process and so at least facilitates the adhesion of the mussel to a variety of substrates, including wood, metal, and mineral surfaces, among others, when submerged in seawater. Embodiments of the orthodontic adhesive system 10 include selected engineered marine mussel proteins or similar components so as to mimic the attachment and/or detachment functionality of the mussel in the oral environment. Exemplary adhesives include those disclosed in U.S. Pub. Nos. 2016/0160097 and 2017/0217999 which are each incorporated by reference herein in their entirety. The engineered marine mussel protein may be synthesized or be genetically engineered.

Figure 7A:
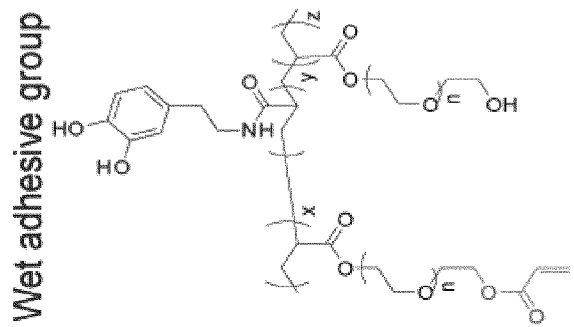
FIG. 7A depicts exemplary wet adhesive groups according to one embodiment of the invention.

With reference to FIG. 7A, in an exemplary embodiment, the engineered marine mussel protein of the orthodontic adhesive system 10 includes a monomer having a catechol moiety and/or a catechol derivative moiety and therefore have similar properties to DOPA, as is shown in (1). The catechol moieties and/or catechol derivative moieties of the orthodontic adhesive system 10 include nitrocatechol or one or more nitrocatechol derivative-containing compounds, which provide chelation, self-polymerization, and crosslinking functionality. By way of further example, FIG. 7A shows an exemplary catechol derivative containing compound having a wet adhesive group that binds to enamel. The wet adhesive group includes one or more functional monomers (FIG. 7C) that crosslink with other components of the adhesive system 10. The functional monomers include at least one of a phosphonate and a cyclic disulfide moiety, both of which can undergo a reaction with a polymerizable group of the monomer.

With reference to FIGS. 2-6, the catechol derivative moiety and the functional monomer of the engineered protein adhesive of the orthodontic adhesive system 10 may be tethered together to form at least a portion of layer 18, 24 with the catechol derivative moiety bonding to the tooth surface 22. This moiety may facilitate adhesion of the monomer to the tooth surface 22 in the absence of prior cleaning, etching, and drying the tooth surface 22. By eliminating one or more of these preparation steps, embodiments of the invention reduce chair time. The reduction in time to bond a single bracket to a tooth may be reduced by about 80%. For example, conventional preparation and adhesive may require as much as 4 minutes per tooth. Embodiments of the invention may reduce that to about 30 seconds per tooth. A typical bonding appointment takes from 2 to 3 hours of patient commitment. Embodiments of the invention greatly reduce the time needed for bonding and is advantageous for at least that reason. For example, according to embodiments of the invention, a clinician may bond orthodontic appliances to a patient's teeth on the same day as an initial consultation. This is not commonly practiced because of the long chair time requirements associated with bonding orthodontic appliances to the patient's teeth. Moreover, the reduction in bonding time, and chair time associated therewith, results in reduced cost for the clinician while increasing potential profitability by increasing the clinician's capacity to see more patients.

In any of the exemplary systems 10 shown in FIGS. 3-6, the monomer of the engineered protein adhesive adheres to the tooth surface 22 and forms a base onto which the orthodontic device is ultimately attached. For example, and with reference to FIG. 3, in one embodiment, the orthodontic adhesive system 10 may include four layers that collectively form the composite layer 24. In that regard, the orthodontic adhesive system 10 may include one or more separately applied layers 26, 28, 30, and 32 that collectively bond the orthodontic bracket 12 to the tooth 14. Each of the components in the layers 26, 28, 30, 32 bonds with components in the other layers and/or with the tooth 14 or the orthodontic bracket 12.

In the exemplary embodiment, the layer 26 is in direct contact with the tooth surface 22. The layer 26 includes a monomer of an engineered mussel protein that has a catechol-like moiety described above. By way of example, the monomer of the engineered mussel protein includes catechol methacrylate. Unlike some conventional orthodontic sealants, the catechol-like moiety forms adhesion networks through hydrogen bonding and metal-ligand complexes with hydroxyapatite without one or more of cleaning, etching, or drying preparation steps. Additionally, the catechol-like moieties may undergo Michael addition with collagen in enamel or in dentin to chemically bond the layer 26 to the tooth surface 22.

Although not shown in FIG. 3, by way of example only, the layer 26 may be on the order of about 100 nanometers thick. The layer 26 may be thicker or thinner than 100 nanometers and may depend on application technique and viscosity of the layer 26. The layer 26 may be very thin relative to the overall thickness of the joint formed by the adhesive system 10 between the bracket body 12 and tooth 14. The layers 28, 30, and 32 may be separately applied on the monomer of layer 26 attached to the tooth surface 22.

The layer 28 may be in direct contact and may chemically bond with the catechol derivative containing monomer that forms the layer 26 before or after that layer cures. In the embodiment shown in FIG. 3, the layer 28 may include a nitrocatechol and nitrocatechol derivative-containing compound (described below) that bonds to the dried monomer that forms the layer 26. In an exemplary embodiment, the layer 28 denatures when exposed to a specific wavelength of light. Thus, at the end of treatment, the clinician can expose the system 10 to that light to denature layer 28. As a result, that layer dissolves and releases the orthodontic bracket 12. The clinician then easily removes the orthodontic bracket 12.

In one embodiment, and with reference to FIG. 3, a sealant may form layer 30. The layer 30 may be in direct contact and may chemically bond with the nitrocatechol and nitrocatechol derivative-containing compound that forms the layer 28 before or after that layer cures. In the embodiment shown in FIG. 3, the layer 30 may be an acrylate-based resin sealant that bonds to the layer 28. In one embodiment, the sealant forming the layer 30 is a commercially available orthodontic sealant, such as Ortho Solo™, available from Kerr Corporation of Orange, Calif.

As shown, the layer 32 may then be directly applied on the layer 30 in a separate application. The layer 32 chemically bonds to the layer 30 and also mechanically bonds to the orthodontic bracket 12. By way of example only, the layer 32 may include a resin, such as a methacrylic resin, which may include an acrylate and/or a methacrylate moiety that chemically bonds with the acrylate-based resin sealant of layer 30 when exposed to a preselected wavelength of light. When applied, the layer 32 may include a photo-initiator to facilitate curing of the layer 32. In one embodiment, the resin is a commercially available orthodontic adhesive, such as Grengloo® or Blugloo, each of which is commercially available from Ormco Corporation of Orange, Calif.

In the case of the layer 32, which may include the photo-initiator, the orthodontic bracket 12 may be pressed against the composite layer 26, 28, 30, and 32 shown in FIG. 3. The adhesive layer 32 may then be cured by exposing it to light, such as visible blue light (e.g., wavelengths of about 450 nm to about 475 nm). This photo-curing process cures at least the layer 32. By way of further example, each of the layers 26, 28, 30, and 32 may be cured at the same time or at different times. The timing of each cure depends on the preferences of the clinician. A clinician may prefer to partially cure the layer 26 to make it tackier and then apply the remaining layers with a final cure of each of the layers 26, 28, 30, and 32 together. When the layers 26, 28, 30, and 32 are cured, the orthodontic adhesive system 10 bonds the orthodontic bracket 12 to the tooth surface 22.

In the exemplary orthodontic adhesive systems 10 shown in FIGS. 4, 5, and 6, the functionalities described above with regard to the layers 26, 28, 30, and 32 may be combined in fewer than four layers. For example, the functionality of layers 28 and 30 may be combined resulting in a three-layer system (FIG. 4). By way of further example, a two-layer system (FIG. 5) may combine the functionality of the catechol derivative moiety of layer 26 with a sealant, such as that described above in layer 30, which may include a nitrocatechol and nitrocatechol derivative-containing compound. In this case, the functionality of layers 26, 28, and 30 of FIG. 3 is present in a layer 40 of FIG. 5. Thus, with reference to FIG. 5, the layer 40 is applied to the tooth surface 22. The moiety of the layer 40 may form adhesion networks through hydrogen bonding and metal-ligand complexes with the enamel at the surface 22 without one or more of cleaning, etching, or drying.

With reference to FIG. 5, a layer 42 may be similar to the layer 32 of FIG. 3. Specifically, the layer 42 may include a resin, such as a methacrylic resin, which may include an acrylate and/or a methacrylate moiety that chemically bonds with a resin of layer 40. The bonding network may be schematically represented by FIG. 7B, described above.

In FIG. 6, in one embodiment, the orthodontic adhesive system 10 includes the single layer 18 having components which combine the functions of the layers 26, 28, 30, and 32 described above. By way of example, a catechol derivative moiety of the layer 18 may form adhesion networks through hydrogen bonding and metal-ligand complexes with enamel without one or more of cleaning, etching, or drying the tooth surface 22. And, the layer 18 may include a debonding compound and a resin, such as a methacrylic resin, which may include an acrylate and/or a methacrylate moiety that chemically bonds with the acrylate-based resin sealant and ultimately a bond is formed between the orthodontic adhesive system 10 and the bracket 12. The figures are not drawn to scale. Thus, while layers 26, 28, 30, and 32 in FIG. 3; layers 26, 30, and 32 in FIGS. 4; 40 and 42 in FIG. 4; and 18 in FIG. 5, are depicted as being uniformly thick in approximately equal thicknesses, embodiments of the invention are not limited to the relative ratios of the thicknesses shown. The thickness of each layer can vary independently of the other layers.

Figure 7B:
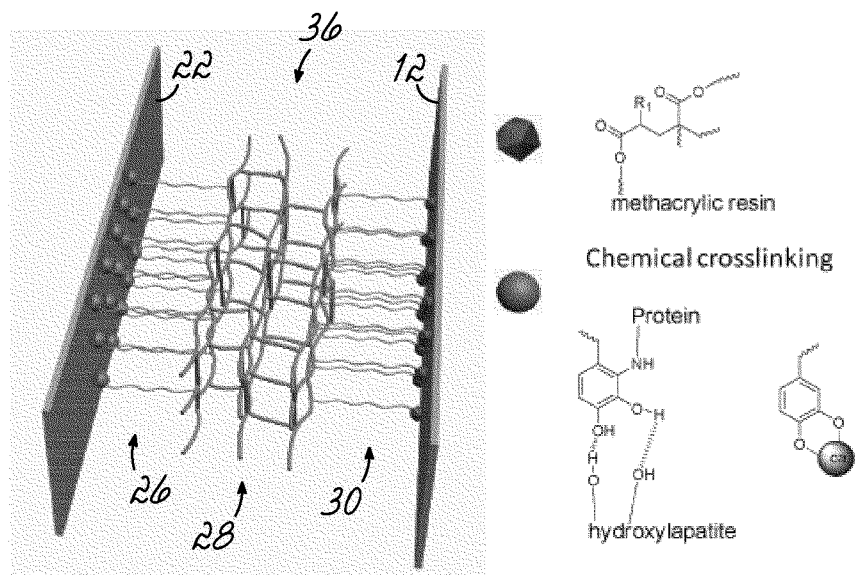
FIG. 7B depicts an enlarged schematic representation of the encircled area 3 of FIG. 2 according to one embodiment of the invention.
Figure 7C:
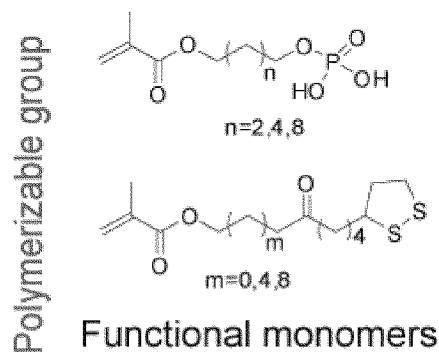
FIG. 7C depicts exemplary monomers including polymerizable groups according to one embodiment of the invention.

An exemplary system orthodontic adhesive system 10 is schematically shown FIG. 7B. In the figure, the catechol derivative containing layer 26 attaches to hydroxyapatite or calcium ions in the enamel or to the dentin on surface 22. The monomer of the layer 26 may bond to the tooth surface 22 and crosslink to sealant of the layer 30 (FIG. 4). The methacrylic resin of the layer 32 crosslinks to the surface of the bracket 12. The region in which the crosslinking occurs may appear as a crosslinking polymer brush at 36.

Figure 8A:
FIG. 8A depicts photocleavage of an exemplary monomer according to one embodiment of the invention.
Figure 8B:
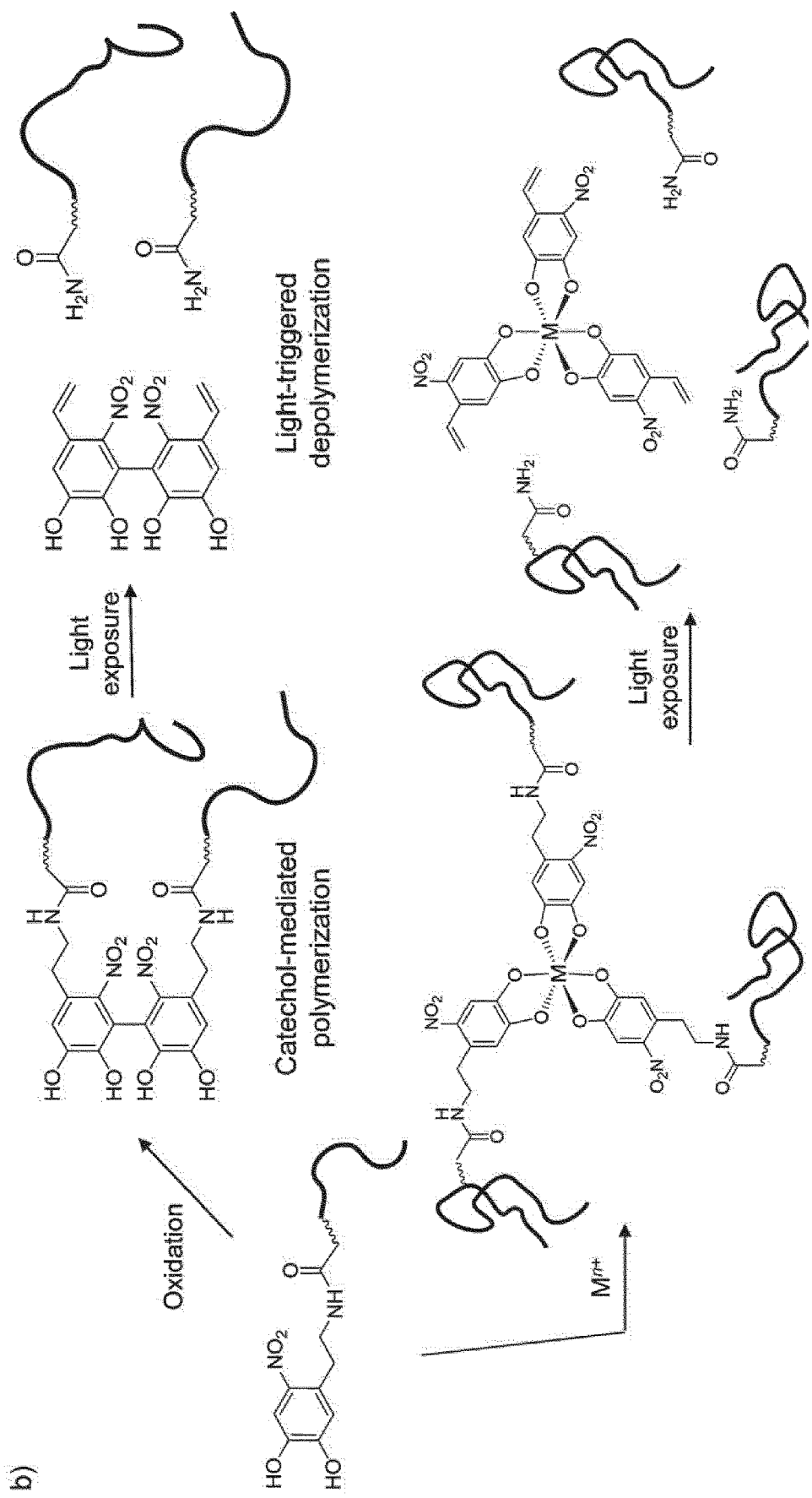
FIG. 8B depicts cross-linking and photocleavage of an exemplary monomer according to one embodiment of the invention.

In an exemplary embodiment and with reference to FIGS. 8A and 8B, nitrocatechol and nitrocatechol derivative-containing compounds may be attached as end groups to a biologically acceptable polymer, such as four-arm star-poly (ethyleneglycol), also known as PEG-$N_{D4}$. The nitrocatechol and nitrocatechol derivative-containing compound may then attach, for example, to the tooth surface 22 or to a separately applied layer of the monomer that has a catechol derivative moiety (e.g., layer 26 of FIG. 3). Similar to the catechol moiety of DOPA, discussed above, nitrocatechol and nitrocatechol derivative-containing compounds may undergo oxidation to form cross-linked networks or undergo metal chelation between non-oxidized nitrocatechol and its derivatives, thus producing a strong bond between two or more nitrocatechol containing compounds. Exemplary nitrocatechol derivative-containing compounds include nitrocatechol, nitrodopamine, nitronorepinephrine, and nitroepinephrine, among others. Not only do some of these compounds mimic the adhesiveness of DOPA to wet surfaces, the catechol derivative moiety, such as nitrocatechol or one or more nitrocatechol derivative-containing compounds, may also be photocleavable.

In that regard, the photocleavable moiety may interact with certain wavelengths of light ("hv" in FIG. 8A). As shown in FIG. 8A, in one embodiment, the monomer including the catechol derivative moiety may be cleaved when exposed to certain wavelengths of light, which may facilitate depolymerization of at least a portion of the orthodontic adhesive system 10. An exemplary photocleavable moiety includes photocleavable bis-methacrylate. Photocleavage of the monomer may be provided by one or more additional moieties pendant to one or more of the nitrocatechol and its derivative-containing compounds described above.

In an exemplary embodiment, and with reference to FIG. 8B, the bond between a leaving group X and an ethyl group pendant to the nitrocatechol moiety is capable of being cleaved with a photon of light having a predetermined energy. By way of example, the photocleavable moiety of the orthodontic adhesive system 10 may be any moiety that is capable of being broken when exposed to light in the infrared (IR) spectrum (i.e., wavelengths of about 700 nm to about 1 mm). Therefore, exposure to, for example, IR light may depolymerize the orthodontic adhesive system 10 and so aid in the debonding of the bracket 12 from the tooth surface 22. It is believed that IR light is advantageous because it passes through both hard (e.g., tooth) and soft (e.g., lips, cheek, and tongue) tissues. The clinician may more easily expose the orthodontic adhesive system 10 to IR light to debond brackets 12 from the teeth 14. Alternatively, the photocleavable moiety may be broken when exposed to light in the ultraviolet (UV) spectrum (i.e., wavelengths of about 10 nm to about 400 nm). Exemplary photocleavable moieties include those reported in Shafiq et al., "Bioinspired Underwater Bonding and Debonding on Demand," 51 *Angew. Chem. Int. Ed.* 4332-35 (2012) (hereinafter "Shafiq"), which is incorporated herein by reference in its entirety.

In one embodiment, the bond between the nitrocatechol derivative moiety and the biologically acceptable polymer may be cleaved upon exposure to light. In this way, the orthodontic adhesive system 10 may be capable of being debonded via light exposure. By way of example, the layer 30 of FIG. 4 may include a photocleavable moiety. In that regard, exposing the bond between the nitrocatechol derivative-containing compound and the biologically acceptable polymer to IR light may weaken or break the bond. By way of example, a typical orthodontic bracket may be bonded to the tooth and achieve a shear strength of from 10 MPa to 20 MPa. IR or UV light exposure may reduce that shear strength to 1 MPa or less. As a result, the nitrocatechol derivative may remain attached to the surface while the biologically acceptable polymer becomes detached from the nitrocatechol derivative moiety. As applied to the embodiment of FIG. 4, for example, when exposed to IR light, the layer 30 may denature, in which case the layer 30 may break down so that the bracket 12 and the layer 32 may be released from the tooth 14. Following debonding, the layer 26 may remain on the tooth surface 22. Thus, during treatment, a dental bracket may be strongly adhered to the teeth of a patient when desired, but then may also be easily removed from the teeth when treatment is completed or when the device needs repositioning or replacement, by exposing the adhesive to an IR light source.

Once treatment is complete, in one embodiment, debonding may include exposing the adhesive to IR light. The orthodontic bracket(s) 12 may fall off or only require a slight application of force for removal. It is thought that any force application in combination with light exposure would be substantially less than conventional forces required to debond orthodontic devices from teeth. In addition to reducing the bonding forces, debonding may minimize or eliminate the need for grinding away residual adhesive once the orthodontic device is removed. In cases where conventional adhesives needed to be removed mechanically (i.e., ground off), patient discomfort from mechanical removal is eliminated using the adhesives of the present invention. Also, emergency appointments may be minimized because the adhesives of the present invention tend to provide higher adhesion strength. For example, bond strength with embodiments of the invention may reach about 15 MPa or more such that accidental debonding may be minimized. These bond strengths may be achieved while also reducing the time it takes to intentionally debond the orthodontic device.

In one embodiment of the invention, the clinician may remove multiple brackets 12, even an entire arch of brackets 12, simultaneously by use of the archwire 16. The clinician may expose the orthodontic adhesive system 10 to IR light. Once at least a portion of the orthodontic adhesive system 10 denatures, the clinician may then pull on the archwire 16 while it is still engaged with each bracket 12 on the arch. The brackets 12 detach while still coupled to the archwire 16. In this way, the clinician may remove each of the brackets 12 with one pull on the archwire 16. This process may leave no residual adhesive on the teeth 14. As another advantage, this prevents unforeseen loss or ingestion of the individual brackets and can significantly reduce chair time, for example, by greater than 90%.

Furthermore, according to embodiments of the invention, the photocleavable moiety may enable reversible adhesion of the orthodontic adhesive system 10 to the tooth surfaces 22. The bonding process of the reversible adhesiveness may even be a type of fast curing (e.g., curing may occur during the few moments when the clinician presses the orthodontic device against the tooth with the catechol derivative-containing compound present on the tooth and the functional monomer present on the restorative part). The adhesion may be reversible in the sense that it can be bonded and then debonded at least twice. This may be useful for when the orthodontic bracket 12 is initially improperly positioned. The orthodontic bracket 12 may then be debonded, reoriented, and then re-bonded to the tooth surface 22. In one embodiment, the adhesiveness of the adhesive may be activated and deactivated during bonding and debonding, respectively. Thus, the adhesive may facilitate an on-demand bonding and on-demand debonding process that permits easy repositioning of the orthodontic device. This may be referred to as a reuseable adhesive system. Advantageously, orthodontic device placement may be perfected without concern that the adhesive polymerizes prior to proper positioning as the adhesive may be selectively bonded and debonded and then rebonded without addition of more adhesive. Clinically, the process of repositioning is common and tedious, thus embodiments of the adhesive described herein saves repositioning time presents a significant shift in the standard of patient care.

In one embodiment of the invention, the orthodontic adhesive may be used in a kit. The kit may include an orthodontic device, such as orthodontic bracket 12, on which the orthodontic adhesive is pre-applied. The kit may include a bubble pack in which the brackets 12 are individually disposed. The clinician may remove the orthodontic brackets 12 individually from the packaging in a particular order and press them to the patient's teeth. The clinician may then cure the pre-applied adhesive with light, such as blue light.

Figure 9:
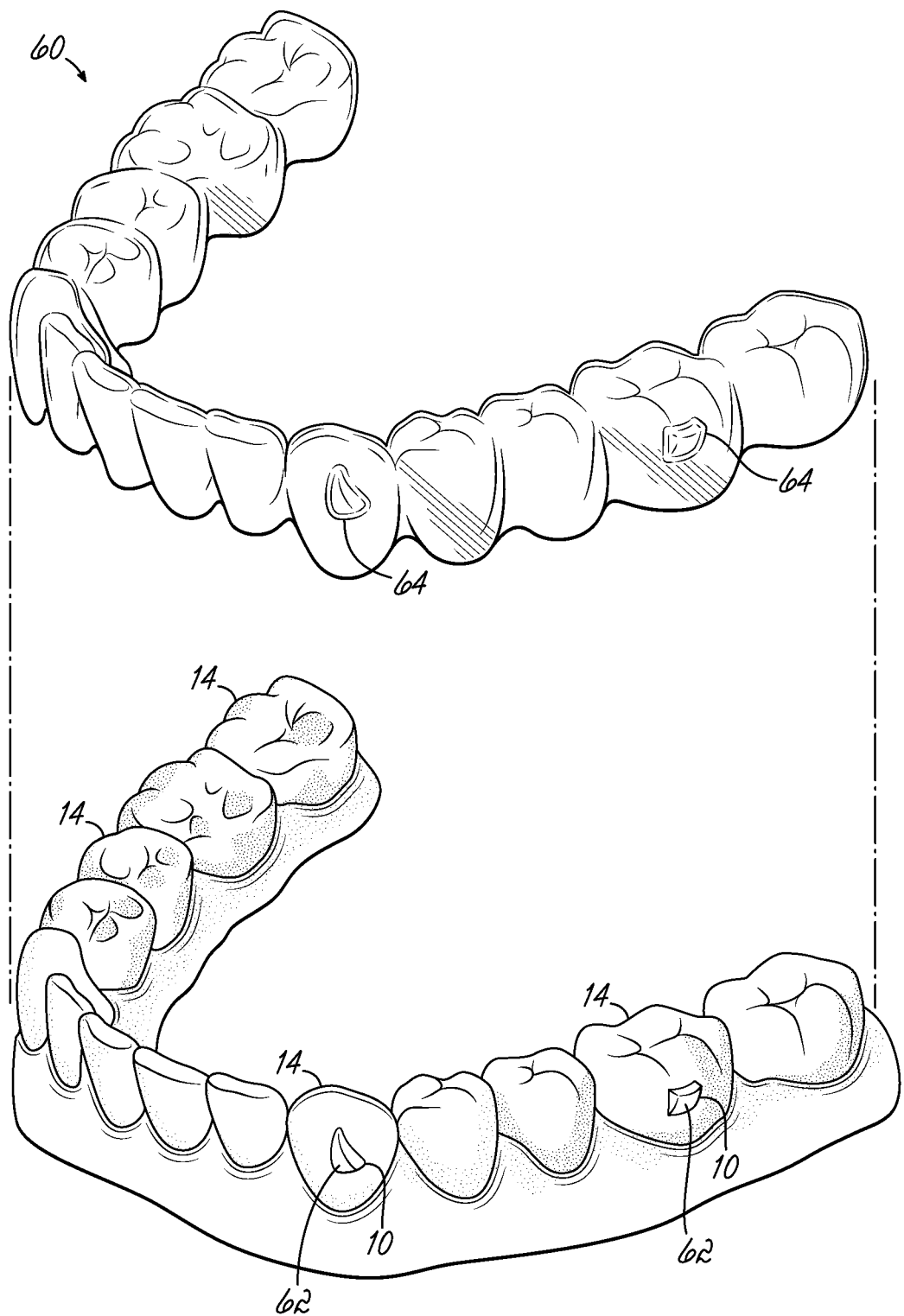
FIG. 9 is a perspective view of one embodiment of the invention with attachments of one embodiment of the invention attached to the teeth of a patient to facilitate orthodontic treatment with an aligner.
Figure 10:
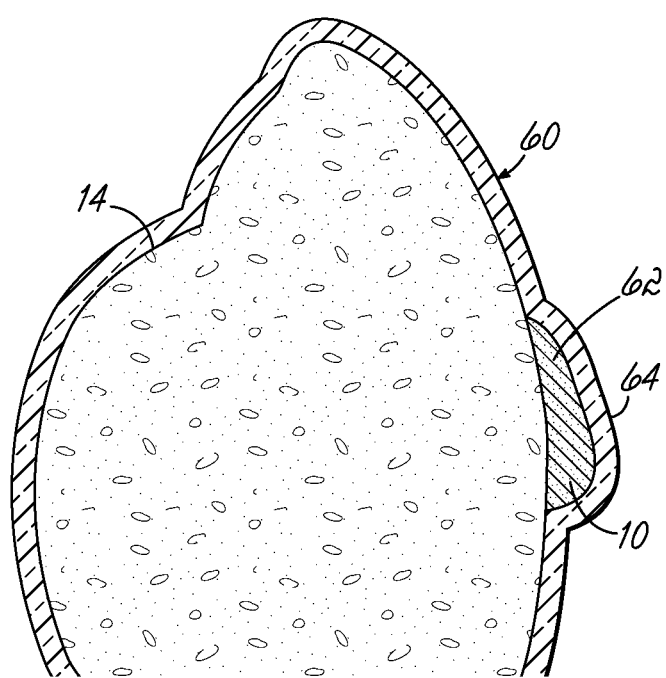
FIG. 10 is a cross section of the aligner and teeth shown in FIG. 9 taken through one of the attachments.

With reference now to FIGS. 9 and 10, in one embodiment, the orthodontic adhesive system 10 may be utilized with other orthodontic appliances, such as an aligner 60. The aligner 60 may be configured to fit over and interact with one or more attachments 62 bonded to one or more teeth 14. Each attachment 62 may be a structure of predetermined shape of the orthodontic adhesive system 10. That is, the orthodontic adhesive system 10 may be formed into a rectangular, square, circular, ellipsoidal or triangular-shaped attachment that is bonded to the tooth surface in a manner similar to that described above respect to the orthodontic brackets 12 (FIG. 1). The attachment 62 may be formed completely of the adhesive system 10.

The aligner 60 may be configured with a corresponding bulge 64 that engages the attachment 62 during orthodontic treatment. Advantageously, each of the attachments 62 may be easily bonded to the tooth surface prior to treatment with an aligner 60 and then may be easily debonded by exposing them to a particular wavelength of light. The attachments 62 may be applied to the tooth with the use of a template (not shown) that allows the clinician to more easily locate the attachment 62 on the patient's tooth. An accurately placed attachment 62 may interact with the corresponding bulge 64 in the aligner 60.

In order to facilitate a more complete understanding of the embodiments of the invention, the following non-limiting example is provided.

EXAMPLE 1

A primer solution of 7.5 wt. % 10-Methacryloxydecyl Dihydrogen Phosphate (MDP) that is modified to have a lower acid value (i.e., purified by removing HCl byproduct), 0.005 wt. % Catechol-methacrylate (CMA) (using eugenol as a backbone for the CMA), and 0.0075 wt. % butylated hydroxytoluene (BHT) in a balance of acetone was applied with a brush to a bovine tooth that was prepared by wiping it with a tissue. No other preparation techniques were used to prepare the surface of the tooth.

A second solution of 10 wt. % photocleavable bis-methacrylate, 0.01 wt. % N,N-di-methyl-amino-ethyl methacrylate (DMAEMA), 0.01 wt % camphoroquinone (CQ), and 0.001 wt % BHT in a balance of acetone was applied with a brush to the dried primer. This forms a debonding layer.

Ortho Solo® sealant is applied to the debonding layer.

Grengloo® adhesive is placed on an orthodontic bracket and then is pressed against the debonding layer with the adhesive in contact with the debonding layer.

The layers were then exposed to a broad spectrum curing light for a few seconds (about 5 seconds or so). Total preparation and bonding time was about 1 minute per sample.

Bond strength as measured for multiple samples was 17 MPa to 19 MPa.

Wire shear bond strength for a sample size of 30 ranged from a high of 36.3 MPa to a low of 17.4 MPa. To demonstrate debonding, a first group of 30 samples assembled as set forth above were exposed to UV light for 10 seconds. Following exposure, the wire shear bond strength ranged from a high of 15.6 MPa to a low of 12.7 MPa. A second group of 30 samples assembled as set forth above were exposed to UV light for 30 seconds. Following exposure, the wire shear bond strength ranged from a high of 9.5 MPa to a low of 0.

COMPARATIVE EXAMPLES

Commercially available adhesives were used to bond the orthodontic bracket to bovine teeth for comparison with Example 1. The manufacturers' instructions were followed for bonding of all commercially available adhesives. A standard tooth preparation technique prior to bonding a bracket to each tooth included, in order: cleaning the tooth with pumice, water rinse, air dry, and apply etching solution.

Two groups of 30 samples each were prepared with each of Orthosolo® and Grengloo® and Transbond™ XT Primer and Transbond™ XT Adhesive available from 3M.

Another group of 30 samples of Self-etching Transbond™ Plus Primer (L-pop delivery) and Transbond™ XT Adhesive were also prepared.

Wire Shear Bond testing of each provided the following results in comparison with Example 1 experimental samples.

| Adhesive System | Wire Shear Bond Strength High (MPa) | Wire Shear Bond Strength Low (MPa) |
| --- | --- | --- |
| Orthosolo/Grengloo ® | 21.2 | 14.3 |
| Transbond XT ™ Primer and Transbond ™ XT Adhesive | 26.2 | 13.6 |
| Transbond ™ XT Plus Primer and Transbond ™ XT Adhesive | 13.6 | 9.1 |
| Example 1 | 36.3 | 17.4 |
| Example 1 after 10 second UV exposure | 15.6 | 12.7 |
| Example 1 after 30 second UV exposure | 9.5 | 0 |

While the present invention has been illustrated by a description of various preferred embodiments and while these embodiments have been described in some detail, it is not the intention of the inventors to restrict or in any way limit the scope of the appended claims to such detail. Additional advantages and modifications will readily appear to those skilled in the art. The various features of the invention may be used alone or in any combination depending on the needs and preferences of the user.

What is claimed is:

1. An orthodontic adhesive system comprising:
   an engineered marine mussel protein including at least one catechol moiety or catechol derivative moiety, and
   a nitrocatechol derivative selected from the group consisting of nitrodopamine, nitronorepinephrine, and nitroepinephrine.

2. The orthodontic adhesive system of claim 1, further comprising catechol-methacrylate.

3. The orthodontic adhesive system of claim 1, further comprising a photocleavable bis-methacrylate.

4. A method of adhering an orthodontic device to a tooth comprising:
   applying a layer of an orthodontic adhesive system to the tooth and/or the orthodontic device, the orthodontic adhesive system comprising:

an engineered marine mussel protein including at least one catechol moiety or catechol derivative moiety, and a nitrocatechol derivative selected from the group consisting of nitrodopamine, nitronorepinephrine, and nitroepinephrine; and affixing the orthodontic device to the tooth with the orthodontic adhesive system situated between the tooth and the orthodontic device.

5. The method of claim 4, wherein the catechol moiety includes catechol-methacrylate.

6. The method of claim 4, further comprising:
applying an acrylate moiety and/or a methacrylate moiety onto the layer.

7. The method of claim 6, wherein the moiety is bis-methacrylate.

8. An attachment for use with an aligner during orthodontic treatment, the attachment comprising:
an engineered marine mussel protein including at least one catechol moiety or catechol derivative moiety, and
a nitrocatechol derivative selected from the group consisting of nitrodopamine, nitronorepinephrine, and nitroepinephrine.

9. A kit comprising:
an orthodontic device; and
an engineered marine mussel protein including at least one catechol moiety or catechol derivative moiety, and
a nitrocatechol derivative selected from the group consisting of nitrodopamine, nitronorepinephrine, and nitroepinephrine.

* * * * *